United States Patent
Schoonebeek et al.

(10) Patent No.: US 10,815,169 B2
(45) Date of Patent: *Oct. 27, 2020

(54) CONVERSION OF MIXED METHANE/ETHANE STREAMS

(71) Applicant: SHELL OIL COMPANY, Houston, TX (US)

(72) Inventors: Ronald Jan Schoonebeek, Amsterdam (NL); Alouisius Nicolaas Renée Bos, Amsterdam (NL); Guus Van Rossum, Amsterdam (NL); Michael Johannes Franciscus Maria Verhaak, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/074,844

(22) PCT Filed: Feb. 2, 2017

(86) PCT No.: PCT/EP2017/052250
§ 371 (c)(1),
(2) Date: Aug. 2, 2018

(87) PCT Pub. No.: WO2017/134164
PCT Pub. Date: Aug. 10, 2017

(65) Prior Publication Data
US 2019/0039972 A1 Feb. 7, 2019

(30) Foreign Application Priority Data

Feb. 4, 2016 (EP) .................................... 16154247

(51) Int. Cl.
*C07C 5/48* (2006.01)
*C07C 7/148* (2006.01)
(Continued)

(52) U.S. Cl.
CPC ............... *C07C 5/48* (2013.01); *B01J 23/002* (2013.01); *B01J 23/688* (2013.01);
(Continued)

(58) Field of Classification Search
CPC ........... C07C 5/48; C07C 27/26; C07C 7/148; C10L 3/10
(Continued)

(56) References Cited

U.S. PATENT DOCUMENTS 4,524,236 A † 6/1985 McCain
7,091,377 B2   8/2006 Borgmeier et al.
(Continued)

FOREIGN PATENT DOCUMENTS

EP   1511563 A2   3/2005
GB   1314613 A    4/1973
(Continued)

OTHER PUBLICATIONS

International Search Report and Written Opinion received for PCT Patent Application No. PCT/EP2017/052250, dated Apr. 7, 2017, 9 pages.
(Continued)

*Primary Examiner* — Thuan D Dang

(57) ABSTRACT

The invention relates to a process for conversion of a stream comprising methane and ethane, comprising converting ethane from a stream comprising methane and ethane, in which stream the volume ratio of methane to ethane is of from 0.005:1 to 100:1, to a product having a vapor pressure at 0° C. lower than 1 atmosphere, resulting in a stream comprising methane and the product having a vapor pressure at 0° C. lower than 1 atmosphere; separating the product having a vapor pressure at 0° C. lower than 1 atmosphere from the stream comprising methane and the product having a vapor pressure at 0° C. lower than 1 atmosphere, resulting in a
(Continued)

stream comprising methane; and chemically converting methane from the stream comprising methane, or feeding methane from the stream comprising methane to a network that provides methane as energy source, or liquefying methane from the stream comprising methane.

23 Claims, 1 Drawing Sheet

(51) Int. Cl.

| | |
|---|---|
| B01J 23/68 | (2006.01) |
| B01J 27/057 | (2006.01) |
| C07D 301/10 | (2006.01) |
| C10G 50/00 | (2006.01) |
| B01J 37/06 | (2006.01) |
| C10L 3/10 | (2006.01) |
| B01J 23/00 | (2006.01) |
| B01J 37/03 | (2006.01) |
| B01J 37/02 | (2006.01) |

(52) U.S. Cl.
CPC .......... *B01J 27/0576* (2013.01); *B01J 37/06* (2013.01); *C07D 301/10* (2013.01); *C10G 50/00* (2013.01); *C10L 3/101* (2013.01); *B01J 37/0236* (2013.01); *B01J 37/03* (2013.01); *B01J 2523/00* (2013.01); *C10G 2300/1081* (2013.01); *Y02P 20/52* (2015.11)

(58) Field of Classification Search
USPC ................ 585/800, 803, 802, 654, 655, 658
See application file for complete search history.

(56) References Cited

U.S. PATENT DOCUMENTS

| | | |
|---|---|---|
| 2004/0147393 A1 | 7/2004 | Hibst et al. |
| 2009/0281345 A1 | 11/2009 | Matusz |
| 2010/0256432 A1 | 10/2010 | Arnold et al. |
| 2012/0222422 A1* | 9/2012 | Nunley ................ C07C 67/055 |
| | | 60/645 |

FOREIGN PATENT DOCUMENTS

| | | |
|---|---|---|
| WO | 03064035 A1 | 8/2003 |
| WO | 2010096909 A1 | 9/2010 |
| WO | 2012101069 A1 | 8/2012 |
| WO | 2012101092 A1 | 8/2012 |
| WO | 2012118888 A2 | 9/2012 |
| WO | 2015057753 A1 | 4/2015 |

OTHER PUBLICATIONS

International Search Report and Written Opinion received for PCT Patent Application No. PCT/EP2016/071948, dated Nov. 21, 2016, 8 pages.

\* cited by examiner
† cited by third party

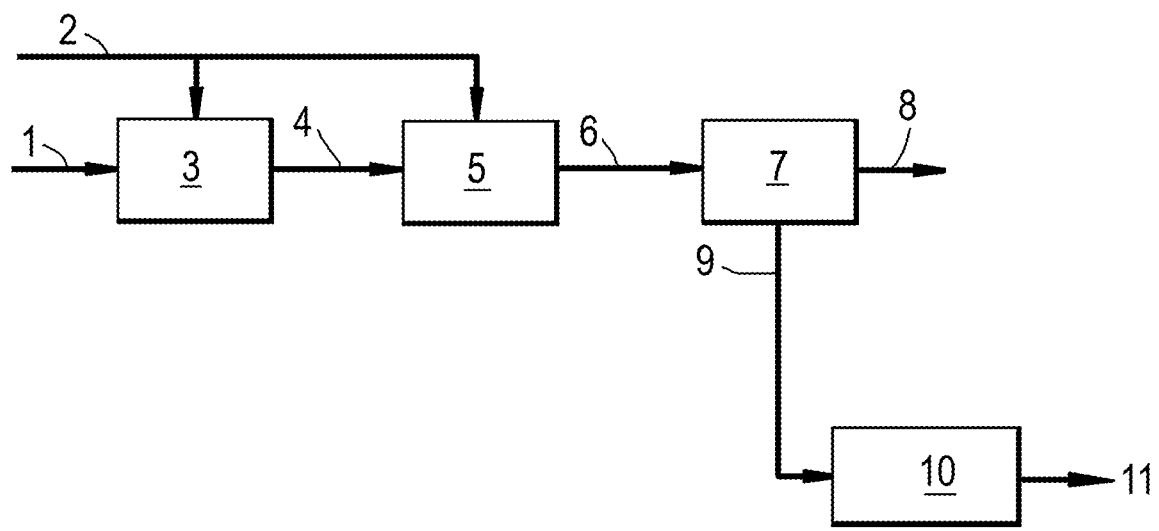

CONVERSION OF MIXED METHANE/ETHANE STREAMS

CROSS REFERENCE TO RELATED APPLICATIONS

This is a national stage application of International Application No. PCT/EP2017/052250, filed 2 Feb. 2017, which claims benefit of priority to European Application No. 16154247.7, filed 4 Feb. 2016.

FIELD OF THE INVENTION

The present invention relates to a process for conversion of a stream comprising methane and ethane.

BACKGROUND OF THE INVENTION

Streams comprising methane and ethane may originate from many sources. For example, natural gas comprises methane and ethane. Each of methane and ethane may have different end uses or may be converted into different chemical products. For example, ethane may be converted into ethylene in a steam cracking process, which ethylene may then be further converted into ethylene derivatives, such as ethylene oxide (EO), ethylbenzene (EB) and polyethylene (PE). However, before such end use or chemical conversion can be effected, methane and ethane need to be separated physically from each other. Typically, such separation is performed in a dedicated "gas plant" resulting in separate streams of methane and ethane for further processing. Such separation is cumbersome since it generally requires cryogenic distillation, wherein a relatively high pressure and a relatively low (cryogenic) temperature are applied to effect the separation of ethane from methane. Such separation is even more cumbersome in a case where the relative amount of ethane is small, as is generally the case for natural gas.

WO2012118888 discloses a process comprising selectively extracting at least one natural gas component from a natural gas stream, which at least one natural gas component may be ethane, by (a) contacting the natural gas stream with a catalyst under conditions that selectively convert the natural gas component into at least one product and (b) separating the product from the remaining components of the natural gas stream.

It may be an objective to provide a technically advantageous, efficient and affordable process for conversion of a stream comprising methane and ethane, which avoids the need for a physical separation of methane and ethane before effecting an end use or a chemical conversion of each of methane and ethane. Further, it may be an objective to provide a technically advantageous process for conversion of a stream comprising methane and ethane, wherein the conversion is relatively high at a certain selectivity or where the selectivity is relatively high at a certain conversion. Such technically advantageous process would preferably result in a lower energy demand and/or lower capital expenditure.

SUMMARY OF THE INVENTION

It was found that one or more of the above-mentioned objectives can be obtained by first converting ethane from a stream comprising methane and ethane to a product having a vapor pressure at 0° C. lower than 1 atmosphere, resulting in a stream comprising methane and the product having a vapor pressure at 0° C. lower than 1 atmosphere, then separating latter product resulting in a stream comprising methane, and finally chemically converting or liquefying methane from the stream comprising methane or feeding said methane to a network that provides methane as energy source.

Advantageously, methane is relatively inert, meaning that said methane remains substantially unconverted and therefore methane can advantageously still be converted into useful chemical products or power after the ethane has been converted.

Accordingly, the present invention relates to a process for conversion of a stream comprising methane and ethane, comprising converting ethane from a stream comprising methane and ethane, in which stream the volume ratio of methane to ethane is of from 0.005:1 to 100:1, preferably of from 0.2:1 to 100:1, more preferably of from 0.5:1 to 100:1, to a product having a vapor pressure at 0° C. lower than 1 atmosphere, resulting in a stream comprising methane and the product having a vapor pressure at 0° C. lower than 1 atmosphere;

separating the product having a vapor pressure at 0° C. lower than 1 atmosphere from the stream comprising methane and the product having a vapor pressure at 0° C. lower than 1 atmosphere, resulting in a stream comprising methane; and chemically converting methane from the stream comprising methane, or feeding methane from the stream comprising methane to a network that provides methane as energy source, or liquefying methane from the stream comprising methane.

BRIEF DESCRIPTION OF THE DRAWINGS

FIG. 1 shows an embodiment of the present invention.

DETAILED DESCRIPTION OF THE INVENTION

In the context of the present invention, in a case where a stream, catalyst or composition comprises two or more components, these components are to be selected in an overall amount not to exceed 100%.

While the processes of the present invention and the streams, catalysts or compositions used in said processes are described in terms of "comprising", "containing" or "including" one or more various described steps and components, respectively, they can also "consist essentially of" or "consist of" said one or more various described steps and components, respectively.".

Within the present specification, by "conversion", reference is made to a "conversion per pass" in the case of a reactor where unconverted reactant(s) from the product stream is (are) recycled to the reactor. In case there is no such recycle, said "conversion" means the conversion in the one and only pass. Further, by said "recycle" reference is made to a recycle over the same reactor wherein a portion of the exit stream (product stream) of said reactor is recycled to said same reactor.

In the present invention, it is preferred that substantially no or only a relatively small amount of methane from the stream comprising methane and ethane is converted. If some of the methane is converted, it may for example be converted to carbon oxides (carbon monoxide and/or carbon dioxide) in case oxygen is present. Preferably, less than 10% of the methane is converted, more preferably less than 5%, more preferably less than 3%, more preferably less than 2%, more preferably less than 1%, more preferably less than 0.5%, most preferably less than 0.1%. For example, if some of the methane is converted, suitably of from 0.01% to 10% may be converted, more suitably of from 0.01% to 5%, more suitably of from 0.01% to 2%, most suitably of from 0.01% to 1%. Further, preferably, more than 80% of the ethane is converted, more preferably more than 85%, more preferably more than 90%, more preferably more than 95%, more preferably more than 98%, more preferably more than 99%, more preferably more than 99.5%, most preferably more than 99.9%. For example, suitably of from 80% to 99.9% of the ethane may be converted, more suitably of from 90% to 99.9%, more suitably of from 95% to 99.9%, most suitably of from 99% to 99.9%.

The above-mentioned selective conversion of ethane, as compared to methane, may be achieved by controlling the reaction conditions, such as temperature, pressure, gas hourly space velocity (GHSV) and/or catalyst reactivity. The reaction conditions should be such that the conversion of ethane is maximized and the conversion of methane is minimized.

In the process of the present invention, the conversion of ethane, as fed to a reactor, may vary widely.

In the present invention, when converting ethane from the stream comprising methane and ethane to a product having a vapor pressure at 0° C. lower than 1 atmosphere, the conversion of ethane is preferably higher than 30%, more preferably of from 50 to 99.9%, more preferably of from 60 to 99.9%, more preferably of from 70 to 99.9%, most preferably of from 70 to 90%. Preferably, said conversion is higher than 30%, more preferably at least 35%, more preferably at least 40%, more preferably at least 45%, more preferably at least 50%, more preferably at least 55%, more preferably at least 65%, more preferably at least 70%, more preferably at least 75%, more preferably at least 80%, most preferably at least 85%. Further, preferably, said conversion is at most 99.9%, more preferably at most 99.5%, more preferably at most 99%, more preferably at most 98%, more preferably at most 95%, more preferably at most 92%, most preferably at most 90%.

In the present invention, preferably, the stream comprising methane and the product having a vapor pressure at 0° C. lower than 1 atmosphere is not recycled to the step, which step may comprise one or multiple conversion steps, wherein ethane from the stream comprising methane and ethane, in which stream the volume ratio of methane to ethane is of from 0.005:1 to 100:1, is converted to a product having a vapor pressure at 0° C. lower than 1 atmosphere. In the latter case, wherein there is no recycle, there is question of a so-called "once-through process". Nevertheless, in the present invention, a relatively small portion of said stream may be recycled. Suitably, the volume ratio of any recycled portion of said stream to the non-recycled portion of said stream is of from 0:1 to 0.5:1, more suitably of from 0:1 to 0.2:1, and is preferably 0:1. Further, suitably, said volume ratio is at most 0.5:1, more suitably at most 0.3:1, more suitably at most 0.2:1, more suitably at most 0.1:1, most suitably at most 0.05:1.

In the present invention, when converting ethane from the stream comprising methane and ethane to a product having a vapor pressure at 0° C. lower than 1 atmosphere, it is preferred that the temperature is of from 100 to 600° C., suitably 200 to 500° C. Further, it is preferred that the pressure is of from 1 to 50 bara (i.e. "bar absolute"), suitably 5 to 25 bara.

In the present process, ethane from the stream comprising methane and ethane is converted to a product having a vapor pressure at 0° C. lower than 1 atmosphere. Suitably, said product may have a vapor pressure lower than 1 atmosphere at a temperature of from 0 to 250° C., more suitably of from 0 to 200° C., more suitably of from 5 to 200° C., most suitably of from 10 to 150° C. As is generally known, the atmospheric pressure boiling point of a liquid (also known as the normal boiling point) is the temperature at which the vapor pressure equals the ambient atmospheric pressure. Therefore, for a product which may be a liquid, the product having a vapor pressure at 0° C. lower than 1 atmosphere has a boiling point equal to or greater than 0° C. Where within the present specification reference is made to a boiling point, the boiling point at atmospheric pressure is meant. Preferably, for a product which may be a liquid, the product having a vapor pressure at 0° C. lower than 1 atmosphere has a boiling point greater than 0° C., more preferably greater than 5° C., most preferably greater than 10° C. Further, said boiling point is preferably at most 250° C., more preferably at most 200° C., most preferably at most 150° C.

In the present invention, the product having a vapor pressure at 0° C. lower than 1 atmosphere may be any product having such vapor pressure. It may be selected from the group consisting of ethylene oxide, acetic acid, ethylbenzene, polyethylene, benzene, toluene, xylenes and vinylacetate. Preferably, in the present invention, the product having a vapor pressure at 0° C. lower than 1 atmosphere is ethylene oxide.

In the present process, ethane from the stream comprising methane and ethane may be converted to a product having a vapor pressure at 0° C. lower than 1 atmosphere in one or multiple conversion steps.

In a first embodiment of the present invention, ethane from the stream comprising methane and ethane is converted to a product having a vapor pressure at 0° C. lower than 1 atmosphere in one conversion step. Suitable examples of such one-step conversions are: 1) converting ethane to acetic acid under oxydehydrogenation conditions (oxidative dehydrogenation; ODH); and 2) converting ethane to aromatics such as benzene, toluene and/or xylenes under aromatization conditions.

In said first embodiment of the present invention, when converting ethane from the stream comprising methane and ethane to a product having a vapor pressure at 0° C. lower than 1 atmosphere in one conversion step, the conversion of ethane is preferably higher than 30%, more preferably of from 50 to 99.9%, more preferably of from 60 to 99.9%, more preferably of from 70 to 99.9%, most preferably of from 70 to 90%. Preferably, said conversion is higher than 30%, more preferably at least 35%, more preferably at least 40%, more preferably at least 45%, more preferably at least 50%, more preferably at least 55%, more preferably at least 65%, more preferably at least 70%, more preferably at least 75%, more preferably at least 80%, most preferably at least 85%. Further, preferably, said conversion is at most 99.9%, more preferably at most 99.5%, more preferably at most 99%, more preferably at most 98%, more preferably at most 95%, more preferably at most 92%, most preferably at most 90%.

In said first embodiment of the present invention, preferably, the stream comprising methane and the product having a vapor pressure at 0° C. lower than 1 atmosphere is not recycled to the step wherein ethane from the stream comprising methane and ethane, in which stream the volume ratio of methane to ethane is of from 0.005:1 to 100:1, is converted to a product having a vapor pressure at 0° C. lower than 1 atmosphere. In the latter case, wherein there is no recycle, there is question of a so-called "once-through process". Nevertheless, in the present invention, a relatively small portion of said stream may be recycled. Suitably, the volume ratio of any recycled portion of said stream to the non-recycled portion of said stream is of from 0:1 to 0.5:1, more suitably of from 0:1 to 0.2:1, and is preferably 0:1. Further, suitably, said volume ratio is at most 0.5:1, more suitably at most 0.3:1, more suitably at most 0.2:1, more suitably at most 0.1:1, most suitably at most 0.05:1.

In particular, said first embodiment of the present invention covers a process, wherein ethane is converted to acetic acid in one conversion step, comprising subjecting a stream comprising methane and ethane, in which stream the volume ratio of methane to ethane is of from 0.005:1 to 100:1, to oxydehydrogenation conditions resulting in a stream comprising methane and acetic acid;

separating acetic acid from the stream comprising methane and acetic acid, resulting in a stream comprising methane; and chemically converting methane from the stream comprising methane, or feeding methane from the stream comprising methane to a network that provides methane as energy source, or liquefying methane from the stream comprising methane.

In a second embodiment of the present invention, ethane from the stream comprising methane and ethane is converted to a product having a vapor pressure at 0° C. lower than 1 atmosphere in two conversion steps. Within said other embodiment, it is preferred that ethane from the stream comprising methane and ethane is first converted to ethylene which is then converted to said product having a vapor pressure at 0° C. lower than 1 atmosphere.

Thus, in said preferred embodiment of said second embodiment, wherein ethane is converted to the product having a vapor pressure at 0° C. lower than 1 atmosphere via ethylene in two conversion steps, the process comprises converting ethane from a stream comprising methane and ethane, in which stream the volume ratio of methane to ethane is of from 0.005:1 to 100:1, to ethylene, resulting in a stream comprising methane and ethylene;

converting ethylene from the stream comprising methane and ethylene to a product having a vapor pressure at 0° C. lower than 1 atmosphere, resulting in a stream comprising methane and the product having a vapor pressure at 0° C. lower than 1 atmosphere;

separating the product having a vapor pressure at 0° C. lower than 1 atmosphere from the stream comprising methane and the product having a vapor pressure at 0° C. lower than 1 atmosphere, resulting in a stream comprising methane; and chemically converting methane from the stream comprising methane, or feeding methane from the stream comprising methane to a network that provides methane as energy source, or liquefying methane from the stream comprising methane.

In said preferred embodiment of said second embodiment, wherein ethane is converted to the product having a vapor pressure at 0° C. lower than 1 atmosphere via ethylene in two conversion steps, when converting ethane from the stream comprising methane and ethane to ethylene in the first conversion step, the conversion of ethane is preferably higher than 30%, more preferably of from 50 to 99.9%, more preferably of from 60 to 99.9%, more preferably of from 70 to 99.9%, most preferably of from 70 to 90%. Preferably, said conversion is higher than 30%, more preferably at least 35%, more preferably at least 40%, more preferably at least 45%, more preferably at least 50%, more preferably at least 55%, more preferably at least 65%, more preferably at least 70%, more preferably at least 75%, more preferably at least 80%, most preferably at least 85%. Further, preferably, said conversion is at most 99.9%, more preferably at most 99.5%, more preferably at most 99%, more preferably at most 98%, more preferably at most 95%, more preferably at most 92%, most preferably at most 90%.

In said preferred embodiment of said second embodiment, wherein ethane is converted to the product having a vapor pressure at 0° C. lower than 1 atmosphere via ethylene in two conversion steps, the stream comprising methane and ethylene resulting from the first conversion step is not recycled to said first conversion step. In the latter case, wherein there is no recycle, there is question of a so-called "once-through process". Nevertheless, in the present invention, a relatively small portion of said stream may be recycled. Suitably, the volume ratio of any recycled portion of said stream to the non-recycled portion of said stream is of from 0:1 to 0.5:1, more suitably of from 0:1 to 0.2:1, and is preferably 0:1. Further, suitably, said volume ratio is at most 0.5:1, more suitably at most 0.3:1, more suitably at most 0.2:1, more suitably at most 0.1:1, most suitably at most 0.05:1.

Suitable examples of such two-step conversions are processes wherein ethane is converted to ethylene in a first conversion step, such as: 1) converting ethane to ethylene under oxydehydrogenation conditions (as further illustrated below); 2) converting ethane to ethylene in a steam cracking process, followed by a second conversion step wherein ethylene is converted into the product having a vapor pressure at 0° C. lower than 1 atmosphere, such as: 1) ethylene oxide by oxidation of ethylene (as further illustrated below); 2) ethylbenzene which can be formed by reaction of ethylene and benzene; 3) polyethylene which can be formed by oligomerization or polymerization of ethylene; 4) aromatics such as benzene, toluene and/or xylenes which are formed by conversion of ethylene into one or more of said aromatics; 5) vinylacetate which can be formed by reaction of ethylene and acetic acid.

In particular, said second embodiment of the present invention covers a process, wherein ethane is converted to ethylene oxide via ethylene in two conversion steps, comprising subjecting a stream comprising methane and ethane, in which stream the volume ratio of methane to ethane is of from 0.005:1 to 100:1, to oxydehydrogenation conditions resulting in a stream comprising methane, ethylene and optionally acetic acid;

converting ethylene from the stream comprising methane, ethylene and optionally acetic acid to a product having a vapor pressure at 0° C. lower than 1 atmosphere, resulting in a stream comprising methane and the product having a vapor pressure at 0° C. lower than 1 atmosphere;

separating the product having a vapor pressure at 0° C. lower than 1 atmosphere from the stream comprising methane and the product having a vapor pressure at 0° C. lower than 1 atmosphere, resulting in a stream comprising methane; and chemically converting methane from the stream comprising methane, or feeding methane from the stream comprising methane to a network that provides methane as energy source, or liquefying methane from the stream comprising methane.

Surprisingly, it has appeared that, by converting ethane from a stream comprising methane and ethane, either directly (via one conversion step) or indirectly (via multiple conversion steps), to a product having a vapor pressure at 0° C. lower than 1 atmosphere, which in the case of a product which can be a liquid corresponds to having a relatively high boiling point, in this case equal to or greater than 0° C., advantageously separation of (unconverted) methane in the below-discussed, next step of the present process is greatly simplified in view of the relatively high boiling point difference between methane (−161° C.) and said product having a boiling point equal to or greater than 0° C. This makes it possible at ambient pressure to separate the methane simply by reducing the temperature to a temperature below the boiling point of the product having a boiling point equal to or greater than 0° C. Advantageously, through the conversion of ethane into a product having a boiling point equal to or greater than 0° C., the subsequent separation of methane from the product having such relatively high boiling point can be performed at a relatively high temperature, for example ambient temperature. In a case where the product having a vapor pressure at 0° C. lower than 1 atmosphere is a solid product which cannot be a liquid, separation is even simpler since the temperature need not be reduced and the methane and the solid product can be separated from each other in any known way.

Thus, in the present process, the product having a vapor pressure at 0° C. lower than 1 atmosphere may be produced from ethane from a stream comprising methane and ethane, via multiple conversion steps as in said second embodiment, wherein ethane is converted to the product having a vapor pressure at 0° C. lower than 1 atmosphere via ethylene in two conversion steps. In general, in such case before the subsequent step wherein the ethylene is further converted into a useful chemical product, the ethylene containing product stream produced in the first conversion step has to be purified. For example, in the latter case, the first conversion step results in a stream comprising methane, ethylene and optionally unconverted ethane. In order to prevent any interference of methane and any unconverted ethane, the ethylene containing product stream would generally be freed from methane and any unconverted ethane, so that a purified ethylene stream would be fed to the subsequent ethylene conversion step. However, having to separate methane and any unconverted ethane from the ethylene is very cumbersome and results in a high expenditure for producing ethylene and relatively high ethylene losses.

Thus, an advantage of the second embodiment of the present process, wherein a product having a vapor pressure at 0° C. lower than 1 atmosphere is produced from ethylene that was produced from a feed containing methane and ethane, is that no methane and no unconverted ethane (if any) have to be separated from the ethylene containing product stream that results from the first conversion step. This results in a much simpler overall process using less separation processes and equipment.

Still further, separation of the stream comprising methane, ethylene and unconverted ethane (if any) resulting from the first conversion step of the second embodiment of the present process is advantageously automatically, and at least partially, effected in the ethylene conversion step wherein ethylene is converted to a product having a vapor pressure at 0° C. lower than 1 atmosphere, which can be separated more easily from the non-converted methane and unconverted ethane (if any), as described above. All these and other advantages also result in a substantial reduction of expenditure, for example savings on costs for compression, refrigeration, etc. needed for separating methane and any unconverted ethane from the ethylene.

A suitable example of the stream comprising methane and ethane to be fed to the first step of the present process, is a gas stream comprising natural gas.

It is envisaged by the present inventors that in the present invention, the stream comprising methane and ethane to be fed to the first step of the present process, is provided by a plant which produces such stream, for example as a side-stream, such as a natural gas production plant, shale gas production plant, natural gas processing plant, Natural Gas Liquids (NGL) recovery and fractionation plant, Liquefied Natural Gas (LNG) production plant and so on, which plants may also be generally referred to as so-called "midstream" plants. Therefore, the present process may be integrated with any one of such midstream plants. However, in the present invention, it is not essential how said stream comprising methane and ethane has been produced.

In addition to methane and ethane, the stream comprising methane and ethane to be fed to the first step of the present process may comprise an inert gas selected from the group consisting of the noble gases and nitrogen ($N_2$). Preferably, such additional inert gas is nitrogen or argon, more preferably nitrogen. A further advantage of the present process is that because of the presence of methane, no such additional inert gas needs to be added or only a substantially smaller amount.

Further, in addition to methane and ethane and any inert gas, the stream comprising methane and ethane to be fed to the first step of the present process may comprise alkanes having 3 or more carbon atoms. Said alkanes having 3 or more carbon atoms may comprise propane and optionally butane. In a case wherein in the present invention, a stream comprising methane, ethane and propane, is subjected to oxydehydrogenation conditions the resulting stream may comprise methane, ethylene and optionally acetic acid, propylene and/or acrylic acid.

In the present process, the volume ratio of methane to ethane in the stream comprising methane and ethane to be fed to the first step of the present process, is of from 0.005:1 to 100:1. Preferably, said volume ratio of methane to ethane is of from 0.2:1 to 100:1, more preferably of from 0.5:1 to 100:1, more preferably 1:1 to 50:1, more preferably 1.5:1 to 30:1, more preferably 2:1 to 20:1, most preferably 3:1 to 10:1. Further, said volume ratio of methane to ethane is at least 0.005:1, or may be at least 0.2:1 or at least 0.3:1 or at least 0.4:1 or at least 0.5:1 or at least 1:1 or at least 1.5:1 or at least 2:1 or at least 2.5:1 or at least 3:1. Still further, said volume ratio of methane to ethane is at most 100:1, or may be at most 70:1 or at most 50:1 or at most 30:1 or at most 20:1 or at most 10:1 or at most 8:1 or at most 7:1 or at most 6:1 or at most 5:1 or at most 4.8:1 or at most 4.5:1 or at most 4:1. In particular, said volume ratio of methane to ethane may be of from 0.005:1 to 4.8:1.

Said ratio of methane to ethane is the ratio at the entrance of a reactor, which reactor may comprise a catalyst bed. Obviously, after entering the reactor, at least part of the ethane gets converted.

Additionally, apart from providing a technically advantageous, efficient and affordable process for conversion of a stream comprising methane and ethane, which avoids the need for a physical separation of methane and ethane before effecting an end use or a chemical conversion of each of methane and ethane, it has also been found that in the presence of methane in said volume ratio of methane to ethane, a relatively high conversion of ethane may be obtained. In particular, this has appeared when subjecting the ethane to oxydehydrogenation conditions resulting in a stream comprising ethylene and optionally acetic acid. More in particular, in such ethane oxydehydrogenation step (ethane ODH step) a relatively high oxygen to ethane volume ratio may be applied, as further described below. That is, the presence of methane makes it possible to employ a relatively high oxygen to ethane volume ratio, while staying in the non-flammability region, so as to convert as much ethane as possible under safe conditions. Additionally, the dilution of the feed to such ethane ODH step by methane, thereby making the ethane concentration relatively low, results in good dissipation of the exothermic heat generated by the ethane ODH step.

Advantageously, through the relatively high conversion of ethane in the present process, the present invention enables the use of a simpler separation section in the production of for example ethylene. For because of the elevated conversion, no separate splitter for splitting ethane from ethylene would be required while generating ethylene with only a low content of the starting ethane. Suitably, such relatively pure ethylene can then be easily further converted into other chemical products, which further conversion is part of the present process.

Further, an advantage obtained in the present process is that because of the positive effect of the presence of methane on the conversion of ethane, also for that reason no prior separation of methane from ethane is needed which results in substantial savings on capital expenditure.

As described above, the present process may comprise subjecting the stream comprising methane and ethane, in which stream the volume ratio of methane to ethane is of from 0.005:1 to 100:1, to oxydehydrogenation conditions resulting in: 1) a stream comprising methane and acetic acid (covered by first embodiment); or 2) a stream comprising methane, ethylene and optionally acetic acid (covered by second embodiment). In said first case, the resulting stream comprises either substantially no ethylene or only a relatively small amount of ethylene. The molar ratio of ethylene to acetic acid in said stream in said first case may be of from 1:9 to 1:200 or of from 1:20 to 1:200 or of from 1:50 to 1:200. In said second case, the resulting stream always comprises ethylene and may comprise acetic acid. The molar ratio of acetic acid to ethylene in said stream in said second case may be of from 1:1 to 1:99 or of from 1:1 to 1:50 or of from 1:1 to 1:20. In both said first case and said second case, advantageously, methane is relatively inert under ethane oxydehydrogenation conditions, meaning that said methane remains substantially unconverted and therefore methane can advantageously still be converted into useful chemical products or power after such oxydehydrogenation.

In a case where in the present process, the stream comprising methane and ethane is first subjected to oxydehydrogenation conditions, the product of such ethane oxidative dehydrogenation step comprises the dehydrogenated equivalent of ethane, that is to say ethylene. Ethylene is initially formed in said ethane oxidative dehydrogenation step. However, in said same step, ethylene may be further oxidized under the same conditions into acetic acid. Thus, the possible products of said oxidative dehydrogenation step comprise ethylene and/or acetic acid.

The above-mentioned ethane oxidative dehydrogenation step may comprise contacting a gas stream comprising oxygen ($O_2$), methane and ethane with a catalyst. Said oxygen is an oxidizing agent, thereby resulting in oxidative dehydrogenation of the ethane. Said oxygen may originate from any source, such as for example air. Thus, in the present invention, oxygen may be provided by introducing high-purity oxygen or air into the process. High-purity oxygen may have a purity greater than 90%, preferably greater than 95%, more preferably greater than 99%, and most preferably greater than 99.4%.

In the above-mentioned ethane oxidative dehydrogenation step, one gas stream comprising oxygen, methane and ethane may be fed to a reactor. Alternatively, two or more gas streams may be fed to the reactor, which gas streams form a combined gas stream inside the reactor. For example, one gas stream comprising oxygen and another gas stream comprising methane and ethane may be fed to the reactor separately.

Ranges for the volume ratio of oxygen to ethane in the gas stream comprising oxygen, methane and ethane which in the above-mentioned ethane ODH step are suitable, are of from 0.1:1 to 7:1, more suitably 0.3:1 to 5:1, more suitably 0.5:1 to 3:1, most suitably 0.5:1 to 2:1.

Said ratio of oxygen to ethane is the ratio at the entrance of a reactor, which reactor may comprise a catalyst bed. Obviously, after entering the reactor, at least part of the oxygen and ethane gets converted.

As mentioned above, in the ethane ODH step a gas stream comprising oxygen, methane and ethane may be contacted with a catalyst. The amount of such catalyst is not essential. Preferably, a catalytically effective amount of the catalyst is used, that is to say an amount sufficient to promote the alkane oxydehydrogenation reaction.

Further, in the above-mentioned ethane ODH step such catalyst may be a mixed metal oxide catalyst containing molybdenum, vanadium, niobium and optionally tellurium as the metals. Thus, in a preferred embodiment of said ethane ODH step, the stream comprising methane and ethane, in which stream the volume ratio of methane to ethane is of from 0.005:1 to 100:1, is subjected to oxydehydrogenation conditions by contacting a gas stream comprising oxygen, methane and ethane with a mixed metal oxide catalyst containing molybdenum, vanadium, niobium and optionally tellurium, resulting in a stream comprising methane and ethylene and/or acetic acid.

In the said ethane ODH step, the above-mentioned mixed metal oxide catalyst containing molybdenum, vanadium, niobium and optionally tellurium may have the following formula:

$$MO_1V_aTe_bNb_cO_n$$

wherein:

a, b, c and n represent the ratio of the molar amount of the element in question to the molar amount of molybdenum (Mo);

a (for V) is from 0.01 to 1, preferably 0.05 to 0.60, more preferably 0.10 to 0.40, more preferably 0.20 to 0.35, most preferably 0.25 to 0.30;

b (for Te) is 0 or from >0 to 1, preferably 0.01 to 0.40, more preferably 0.05 to 0.30, more preferably 0.05 to 0.20, most preferably 0.09 to 0.15;

c (for Nb) is from >0 to 1, preferably 0.01 to 0.40, more preferably 0.05 to 0.30, more preferably 0.10 to 0.25, most preferably 0.14 to 0.20; and n (for O) is a number which is determined by the valency and frequency of elements other than oxygen.

In said ethane ODH step, the above-mentioned mixed metal oxide catalyst containing molybdenum, vanadium, niobium and optionally tellurium is a solid, heterogeneous catalyst. Inside a reactor, this heterogeneous catalyst makes up a catalyst bed through which the gas stream comprising oxygen, methane and ethane is sent.

In the above-mentioned ethane ODH step, typical pressures are 1 to 50 bara (i.e. "bar absolute"), suitably 5 to 25 bara, and typical temperatures (catalyst operating temperature or catalyst bed temperature) are 100-600° C., suitably 200-500° C. Advantageously, a relatively high pressure, up to 50 or 25 bara, may be applied which results in smaller volumes and less compression needs.

In general, the product stream resulting from the above-mentioned ethane ODH step comprises water in addition to the desired product. Water may easily be separated from said product stream, for example by cooling down the product stream from the reaction temperature to a lower temperature, for example room temperature, so that the water condenses and can then be separated from the product stream. In case any acetic acid is formed in said ethane ODH step, the acetic acid would be separated at the same time together with the water. In a preferred embodiment, wherein the stream resulting from said ethane ODH step comprises methane, optionally ethylene, water and optionally acetic acid, said water and optional acetic acid are preferably removed from said stream by subjecting said stream to a condensation treatment, for example by cooling down said stream to a temperature in the range of from 0 to 50° C., suitably 10 to 40° C. or 10 to 30° C.

Examples of oxydehydrogenation processes, including catalysts and other process conditions, are for example disclosed in above-mentioned US7091377, WO2003064035, US20040147393, WO2010096909 and US20100256432, the disclosures of which are herein incorporated by reference.

The stream resulting from the above-mentioned ethane ODH step, which comprises methane, optionally ethylene and optionally acetic acid, may additionally comprise unconverted ethane.

In the second embodiment of the present process, wherein in a first conversion step ethane is converted to ethylene, resulting a stream comprising methane and ethylene, said ethylene from the stream comprising methane and ethylene is converted in a second conversion step to a product having a vapor pressure at 0° C. lower than 1 atmosphere, preferably after removing any water and acetic acid as described above in relation to the case where the first conversion step is an ethane ODH step, resulting in a stream comprising methane and the product having a vapor pressure at 0° C. lower than 1 atmosphere.

In the above-mentioned ethylene conversion step (second conversion step), part of the methane may be separated before ethylene is converted to the product having a vapor pressure at 0° C. lower than 1 atmosphere. The methane may be separated by means of distillation. Where such separation is performed, it is preferably performed after having removed any water and acetic acid as described above in relation to the case where the first conversion step is an ethane ODH step. However, advantageously, in the present process, such methane separation step may be omitted.

The stream resulting from the above-mentioned ethylene conversion step, which stream comprises methane and the product having a vapor pressure at 0° C. lower than 1 atmosphere, may additionally comprise unconverted ethane and/or unconverted ethylene.

Further, in the present process the product having a vapor pressure at 0° C. lower than 1 atmosphere is separated from the stream comprising methane and the product having a vapor pressure at 0° C. lower than 1 atmosphere, resulting in a stream comprising methane. Said separation may be performed in any way. In a case where the product having a vapor pressure at 0° C. lower than 1 atmosphere can be a liquid and has a boiling point equal to or greater than 0° C., said separation may be performed by reducing the temperature to a temperature below the boiling point of the product having a boiling point equal to or greater than 0° C., followed by separation of the liquid and gas phases. Such separation involving cooling can be performed in a so-called "knockout drum". In a case where the product having a vapor pressure at 0° C. lower than 1 atmosphere cannot be a liquid and is a solid, said separation is performed by separation of the solid and gas phases.

Preferably, in a case where in the present invention the above-mentioned ethane ODH step is followed by the above-mentioned ethylene conversion step, ethylene is converted into ethylene oxide and the present process comprises subjecting a stream comprising methane and ethane, in which stream the volume ratio of methane to ethane is of from 0.005:1 to 100:1, to oxydehydrogenation conditions resulting in a stream comprising methane, ethylene and optionally acetic acid;

subjecting ethylene and methane from the stream comprising methane, ethylene and optionally acetic acid to oxidation conditions resulting in a stream comprising methane and ethylene oxide;

separating ethylene oxide from the stream comprising methane and ethylene oxide, resulting in a stream comprising methane; and chemically converting methane from the stream comprising methane, or feeding methane from the stream comprising methane to a network that provides methane as energy source, or liquefying methane from the stream comprising methane.

Accordingly, the present invention also relates to a process for the production of ethylene oxide, comprising the above-mentioned steps.

Generally, in the above-mentioned ethylene oxide production process, a ballast gas would have to be added. For in the oxidation of ethylene an oxidizing agent, such as high-purity oxygen or air, is required. Because an oxidizing agent is required, it is important to control the safe operability of the reaction mixture. Nitrogen may be utilized as such ballast gas. One function of a ballast gas is thus to control this safe operability. It is very cumbersome to provide such ballast gas and feed it to the ethylene oxidation unit, which results in a high expenditure for producing ethylene oxide.

Thus, in addition in a case where the ethylene conversion step is an ethylene oxidation step, the non-separated methane and unconverted ethane (if any) advantageously function as ballast gases in the next ethylene oxidation step so that no or substantially less additional ballast gas, such as nitrogen, needs to be added. This results in a much simpler and more efficient ethylene oxidation process.

In the above-mentioned ethylene oxide production process, the step of subjecting the stream comprising methane and ethane, in which stream the volume ratio of methane to ethane is of from 0.005:1 to 100:1, to oxydehydrogenation conditions resulting in a stream comprising methane, ethylene and optionally acetic acid, is performed in the same way as described above in general for an ethane ODH step.

Further, the stream resulting from the oxydehydrogenation step in the above-mentioned ethylene oxide production process, which stream may comprise methane, ethylene, water and optionally acetic acid, may be subjected to a condensation treatment as described above in general for an ethane ODH step, such as to remove water and any acetic acid therefrom.

Still further, as already referred to above, between the above-mentioned ethane ODH step and ethylene oxidation step (an ethylene conversion step), part of the methane may be separated, for example by means of distillation, preferably after having removed any water and acetic acid. However, advantageously, in the above-mentioned ethylene oxide production process, such methane separation step may be omitted.

The stream resulting from the above-mentioned ethylene conversion step (e.g. ethylene oxidation step) which comprises ethylene oxide and methane, may additionally comprise unconverted ethane and/or unconverted ethylene.

The ethylene oxidation step in the above-mentioned ethylene oxide production process results in a stream comprising ethylene oxide, methane, optionally unconverted ethylene and optionally unconverted ethane from the preceding oxydehydrogenation step. The ethylene oxide can be recovered easily from such stream by means of methods known to the skilled person. That is to say, ethylene oxide may be separated from said stream resulting in a stream comprising methane, optionally unconverted ethylene and optionally unconverted ethane. After ethylene oxide is separated from said stream, any carbon dioxide may be removed. That is to say, either part or all carbon dioxide is removed. Said carbon dioxide may be produced in the ethylene oxide production step and/or may be produced in the oxydehydrogenation step. Ways of removing carbon dioxide, such as a caustic or amine wash, are known to the skilled person. Another advantage of the above-mentioned ethylene oxide production process is that any carbon dioxide produced in the oxydehydrogenation step does not have to be removed before the ethylene oxidation step. Such carbon dioxide removal can be postponed till after said ethylene oxidation step.

In the ethylene oxide production step of the above-mentioned ethylene oxide production process, methane, ethylene and any unconverted ethane from the stream resulting from the oxydehydrogenation step are contacted with an oxidizing agent, for example in the form of high-purity oxygen or air, preferably high-purity oxygen which may have a purity greater than 90%, preferably greater than 95%, more preferably greater than 99%, and most preferably greater than 99.4%. Suitable reaction pressures in the ethylene oxide production step of the above-mentioned ethylene oxide production process are 0.1-30 bar, more suitably 1-20 bar, most suitably 2-10 bar. Suitable reaction temperatures in said step are 100-400° C., more suitably 200-300° C.

An additional advantage of the above-mentioned ethylene oxide production process is that there is no need to remove remaining oxidizing agent, if any, from the product stream resulting from the oxydehydrogenation step, because oxidizing agent is needed any way in the subsequent production of ethylene oxide. For it is cumbersome to eliminate unreacted oxygen from an ethane oxydehydrogenation product stream.

Further, advantageously, the same source of oxidizing agent as used for feeding oxidizing agent to the ethylene oxide production step of the above-mentioned ethylene oxide production process, can be used for feeding oxidizing agent to the ethane oxydehydrogenation step of that same process.

Further, it is preferred that in the ethylene oxide production step of the above-mentioned ethylene oxide production process, the methane, ethylene and any unconverted ethane are contacted with a catalyst, preferably a silver containing catalyst. A typical reactor for the ethylene oxide production step consists of an assembly of tubes that are packed with catalyst. A coolant may surround the reactor tubes, removing the reaction heat and permitting temperature control.

In case a silver containing catalyst is used in the ethylene oxide production step of the above-mentioned ethylene oxide production process, the silver in the silver containing catalyst is preferably in the form of silver oxide. Preferred is a catalyst comprising particles wherein silver is deposited on a carrier. Suitable carrier materials include refractory materials, such as alumina, magnesia, zirconia, silica and mixtures thereof. The catalyst may also contain a promoter component, e.g. rhenium, tungsten, molybdenum, chromium, nitrate- or nitrite-forming compounds and combinations thereof. Preferably, the catalyst is a pelletized catalyst, for example in the form of a fixed catalyst bed, or a powdered catalyst, for example in the form of a fluidized catalyst bed.

The nature of the ethylene oxidation catalyst, if any, is not essential in terms of obtaining the advantages of the present invention as described herein. The amount of the ethylene oxidation catalyst is neither essential. If a catalyst is used, preferably a catalytically effective amount of the catalyst is used, that is to say an amount sufficient to promote the ethylene oxidation reaction.

Examples of ethylene oxidation processes, including catalysts and other process conditions, are for example disclosed in US20090281345 and GB1314613, the disclosures of which are herein incorporated by reference. All of these ethylene oxidation processes are suitable for the ethylene oxidation step of the above-mentioned ethylene oxide production process.

Still further, any unconverted ethylene and/or any carbon oxides (carbon monoxide and/or carbon dioxide) in the final stream comprising methane may be hydrogenated resulting in ethane and methane, respectively. Therefore, optionally in the present invention, the stream comprising methane resulting from separating the product having a vapor pressure at 0° C. lower than 1 atmosphere from the stream comprising methane and the product having a vapor pressure at 0° C. lower than 1 atmosphere, additionally comprises unconverted ethylene and/or carbon oxides and is subjected to hydrogenation resulting in a stream comprising methane and optionally ethane. This optional hydrogenation step may be carried out in any known way. Preferably, the pressure is greater than 1 bar and the temperature is higher than 100° C. As hydrogenation catalyst, a nickel, palladium or platinum containing catalyst may be used.

In the final step of the present process for conversion of a stream comprising methane and ethane, methane from the above-mentioned final stream comprising methane, possibly followed by a hydrogenation step as described above, is chemically converted or liquefied or fed to a network that provides methane as energy source.

The above-mentioned chemical conversion of methane may be any chemical conversion. Said methane may be converted into ethylene by oxidative coupling of methane. Further, said methane may be converted into aromatics such as benzene, toluene and/or xylenes under aromatization conditions. Still further, said methane may be converted into syngas which may then be further converted into paraffins or methanol.

The above-mentioned liquefaction of methane involves compressing methane under high pressure, so that it becomes a liquid, such that the methane can be more easily transported due to a lower volume. Such use may help in making so-called liquid natural gas (LNG).

The above-mentioned feeding of methane to a network that provides methane as energy source may involve any network, including domestic use and industrial use. Before such feeding, the pressure of the methane containing stream may be adjusted.

An example of the second embodiment of the present invention, wherein ethylene from a stream resulting from an ethane oxydehydrogenation step is converted into ethylene oxide, is shown in FIG. 1.

In the flow scheme of FIG. 1, stream 1 comprising methane and ethane is fed to oxydehydrogenation unit 3. Stream 2 comprising an oxidizing agent is also fed to oxydehydrogenation unit 3. Stream 4 comprising methane and ethylene leaving oxydehydrogenation unit 3 is fed to ethylene oxide production unit 5. Stream 4 also comprises water and optionally acetic acid which are removed in a water separation unit (not shown in FIG. 1). Optionally, stream 4 is subjected to hydrotreatment in a hydrotreater unit (not shown in FIG. 1) to convert any acetylene present, before entering ethylene oxide production unit 5. Further, stream 2 comprising an oxidizing agent is fed to ethylene oxide production unit 5. Stream 6 comprising ethylene oxide and methane leaving ethylene oxide production unit 5 is sent to ethylene oxide separation unit 7. Ethylene oxide is recovered via stream 8 leaving ethylene oxide separation unit 7. And methane is recovered via stream 9 leaving ethylene oxide separation unit 7. Said stream 9 comprising methane may be used without any further treatment in the final step of the present invention (not shown in FIG. 1), comprising chemically converting or liquefying methane from said stream comprising methane or feeding said methane to a network that provides methane as energy source. Alternatively, said stream 9 may first be subjected to hydrogenation in a hydrogenation unit 10 to convert any unconverted ethylene to ethane and/or to convert any carbon oxides (carbon monoxide and/or carbon dioxide) to methane, resulting in a stream 11 comprising methane and possibly some ethane. Further, optionally, stream 9 may comprise carbon dioxide which may be removed in a carbon dioxide removal unit (not shown in FIG. 1) before stream 9 is sent to hydrogenation unit 10 and/or before methane from stream 9 is chemically converted or liquefied or fed to a network that provides methane as energy source.

The ethane ODH step of the above-described embodiment of present process, wherein ethane from a stream comprising methane and ethane is converted to ethylene under oxydehydrogenation conditions, is further illustrated by the following Examples.

EXAMPLES (A) Preparation of the Catalyst

A mixed metal oxide catalyst containing molybdenum (Mo), vanadium (V), niobium (Nb) and tellurium (Te) was prepared, for which catalyst the volume ratio of said 4 metals was $Mo_1V_{0.29}Nb_{0.17}Te_{0.12}$.

Two solutions were prepared. Solution 1 was obtained by dissolving 15.8 g of ammonium niobate oxalate and 4.0 g of anhydrous oxalic acid in 160 ml of water at room temperature. Solution 2 was prepared by dissolving 35.6 g of ammonium heptamolybdate, 6.9 g of ammonium metavanadate and 5.8 g of telluric acid ($Te(OH)_6$) in 200 ml of water at 70° C. 7.0 g of concentrated nitric acid was then added to solution 2. The 2 solutions were combined which yielded an orange gel-like precipitate. The mixture was evaporated to dryness with the aid of a rotating evaporator ("rotavap") at 50° C.

The dried material was further dried in static air at 120° C. for 16 hours, milled to a fine powder and then calcined in static air at a temperature of 300° C. for 5 hours. After the air calcination, the material was further calcined in a nitrogen ($N_2$) stream at 600° C. for 2 hours. Then the material was treated with an aqueous 5% oxalic acid solution at 80° C. and filtered and dried at 120° C.

The dried catalyst powder was pressed into pills which pills were then milled. The milled material was then sieved using a sieve having a mesh size of 40-80 mesh. The sieved material having a size of 40-80 mesh was then used in the ethane oxidative dehydrogenation experiments described below.

(B) Catalytic Oxidative Dehydrogenation of Ethane

In Example 1, the catalyst thus prepared was used in an experiment involving ethane oxidative dehydrogenation within a small-scale testing unit comprising a vertically oriented, cylindrical, quartz reactor having an inner diameter of 2.9 mm. 673 mg of the catalyst were loaded in the reactor. The catalyst bed height was 5.7 cm.

In the experiment of Example 1, a gas stream comprising 10.3 vol. % of ethane, 7.5 vol. % of oxygen ($O_2$), 74.5 vol. % of methane ($CH_4$) and 7.7 vol. % of nitrogen ($N_2$) was fed to the top of the reactor and then sent downwardly through the catalyst bed to the bottom of the reactor. Said gas stream was a combined gas stream comprising a flow of ethane, a flow of oxygen, a flow of methane and a flow of nitrogen having a combined total flow rate of 7.8 Nl/hr. "Nl" stands for "normal litre" as measured at standard temperature and pressure, namely 32° F. (0° C.) and 1 bara (100 kPa).

The temperature and pressure in the reactor and the volume ratio of oxygen to ethane and the volume ratio of methane to ethane in the feedstream are shown in Table 1 below for the experiments of Example 1.

The conversion of ethane, the conversion of oxygen and the product composition were measured with a gas chromatograph (GC) equipped with a thermal conductivity detector (TCD) and with another GC equipped with a flame ionization detector. The water and any acetic acid from the reaction were trapped in a quench pot. In Table 1 below, the experimental results (conversion of ethane, conversion of oxygen and the selectivity towards ethylene) for Example 1 are also shown.

TABLE 1

| Ex. | Temperature (° C.) | Pressure (bara) | Volume ratio $O_2:C_2H_6$ | Volume ratio $CH_4:C_2H_6$ |
|---|---|---|---|---|
| 1 | 400 | 8 | 0.73:1 | 7.2:1 |

| | Conversion[1] of ethane (%) | Conversion[1] of oxygen (%) | Selectivity to ethylene (%) |
|---|---|---|---|
| 1 | 70 | 90 | 85 |

[1]= conversion per pass

From the results in Table 1, it appears that advantageously in Example 1, wherein methane is present in the stream comprising ethane that is subjected to oxydehydrogenation conditions in a volume ratio of methane to ethane of from 0.005:1 to 100:1, which is in accordance with the present invention, the conversion of ethane is relatively high, at a relatively high selectivity towards ethylene Thus, in Example 1, it has been found that in the presence of methane in said volume ratio of methane to ethane, a relatively high conversion of ethane into ethylene and optional acetic acid is obtained, while maintaining a relatively high selectivity to ethylene. Further, a relatively high oxygen to ethane volume ratio may be applied in the present invention. In Example 1, it was possible to raise said volume ratio of oxygen to ethane to 0.73. That is, the presence of methane, in a volume ratio of methane to ethane of from 0.005:1 to 100:1, makes it possible to employ a relatively high oxygen to ethane volume ratio, while staying in the non-flammability region, so as to convert as much ethane as possible under safe conditions.

(C) Production of Ethylene Oxide from a Stream Comprising Ethylene, Ethane and Methane The stream produced in the above-mentioned experiment involving ethane oxidative dehydrogenation (ethane ODH) comprised ethylene, ethane and methane. Such stream comprising the latter components was used in the following experiments wherein ethylene oxide (EO) was produced.

In the present EO production experiments, ethylene was oxidized into EO over a silver and rhenium containing catalyst prepared according to EP1511563A2 using air as a source of oxygen (oxidizing agent) and using ethyl chloride (EC) as moderator. Also the testing was done in a similar way as described in EP1511563A2 with some differences described below.

For standard EO plant process conditions, the inlet gas stream would typically be comprised of 15 to 35 vol. % of ethylene, 5 to 9 vol. % of oxygen, 0.5 to 5 vol. % of carbon dioxide, 1 to 10 parts per million by volume (ppmv) of EC, the balance comprising inerts, i.e. methane, nitrogen (originating from the air that was used as the source of oxygen) as well as small amounts of argon and ethane. Typically, the operating pressure would be of from 15 to 25 bar and the temperature would be of from 190 to 280° C. Typically, the conversion of ethylene may be as low as 5 to 20%, because most of the unconverted ethylene is recycled in a conventional EO plant.

For the EO production experiments in these Examples in accordance with the present invention, an inlet gas stream was used that simulates the exit stream of a preceding ethane ODH process in accordance with the present invention. The inlet stream in the present EO production experiments was significantly different from the above-mentioned inlet stream for a standard EO process, and comprised 5.5 vol. % of ethylene, 10 vol. % of oxygen ($O_2$), 0.6 vol. % of ethane, 2.0 vol. % of carbon dioxide ($CO_2$), a variable amount of EC moderator, the balance being above-mentioned inerts. A further difference was that the pressure was reduced to 5.5 bar.

The present EO production experiments were performed at various levels of gas hourly space velocity (GHSV). Further, the conversion of ethylene was varied by varying the temperature. The conversion of ethylene was driven to higher values than normally applied for standard EO plant conditions. For each experiment, the EC concentration was fine tuned within the range of from 15 to 25 ppmv to obtain maximum selectivity.

Said various GHSV and temperatures and the results of the present EO production experiments are shown in Table 2 below. These results show that even at a relatively low operating pressure and a relatively low ethylene partial pressure, high conversions of ethylene can be achieved at good selectivities to ethylene oxide.

TABLE 2

| GHSV (Nl/l · h) | Temperature (° C.) | Conversion[1] of ethylene (%) | Selectivity to ethylene oxide (%) |
|---|---|---|---|
| 1000 | 220 | 68 | 74 |
| 500 | 215 | 82 | 65 |
| 1000 | 230 | 92 | 63 |
| 2000 | 230 | 82 | 70 |

[1]= conversion per pass

That which is claimed is:

1. A process for conversion of a stream comprising methane and ethane, comprising
    converting ethane from a stream comprising methane and ethane, in which stream the volume ratio of methane to ethane is of from 0.005:1 to 100:1 to a product having a vapor pressure at 0° C. lower than 1 atmosphere, resulting in a stream comprising methane and the product having a vapor pressure at 0° C. lower than 1 atmosphere comprising ethylene oxide converted from ethylene produced as an intermediate product of the conversion step;
    separating the product having a vapor pressure at 0° C. lower than 1 atmosphere from the stream comprising methane and the product having a vapor pressure at 0° C. lower than 1 atmosphere, resulting in a stream comprising methane; and
    chemically converting methane from the stream comprising methane or feeding methane from the stream comprising methane to a network that provides methane as energy source, or liquefying methane from the stream comprising methane.

2. The process according to claim 1, wherein when converting ethane to the product having a vapor pressure at 0° C. lower than 1 atmosphere, the conversion of ethane is higher than 30%.

3. The process according to claim 1, wherein the volume ratio of any recycled portion of the stream comprising methane and the product having a vapor pressure at 0° C. lower than 1 atmosphere to the non-recycled portion of said stream is of from 0:1 to 0.5:1.

4. The process according to claim 1, comprising
    subjecting a stream comprising methane and ethane, in which stream the volume ratio of methane to ethane is of from 0.005:1 to 100:1 to oxydehydrogenation conditions resulting in a stream comprising methane, ethylene and optionally acetic acid;
    converting ethylene from the stream comprising methane, ethylene and optionally acetic acid to a product having a vapor pressure at 0° C. lower than 1 atmosphere, resulting in a stream comprising methane and the product having a vapor pressure at 0° C. lower than 1 atmosphere;
    separating the product having a vapor pressure at 0° C. lower than 1 atmosphere from the stream comprising methane and the product having a vapor pressure at 0° C. lower than 1 atmosphere, resulting in a stream comprising methane; and
    chemically converting methane from the stream comprising methane or feeding methane from the stream comprising methane to a network that provides methane as energy source, or liquefying methane from the stream comprising methane.

5. The process according to claim 4, wherein when subjecting the stream comprising methane and ethane to oxydehydrogenation conditions, the conversion of ethane is higher than 30%.

6. The process according to claim 4, wherein the volume ratio of any recycled portion of the stream comprising methane, ethylene and optionally acetic acid resulting from the first conversion step to the non-recycled portion of said stream is of from 0:1 to 0.5:1.

7. The process according to claim 4, wherein the stream comprising methane and ethane has a volume ratio of methane to ethane is from 0.2:1 to 100:1.

8. The process according to claim 4, wherein the stream comprising methane and ethane has a volume ratio of methane to ethane from 0.5:1 to 100:1.

9. The process according to claim 4, wherein the conversion of ethane is from 50 to 99.9%.

10. The process according to claim 4, wherein the conversion of ethane is from 60 to 99.9%.

11. The process according to claim 4, wherein the conversion of ethane is from 70 to 99.9%.

12. The process according to claim 4, wherein the conversion of ethane is from 70 to 90%.

13. The process according to claim 4, wherein the volume ratio of any recycled portion of the stream comprising methane and the product having a vapor pressure at 0° C. lower than 1 atmosphere to the non-recycled portion of said stream is 0:1 to 0.2:1.

14. The process according to claim 4, wherein the volume ratio of any recycled portion of the stream comprising methane and the product having a vapor pressure at 0° C. lower than 1 atmosphere to the non-recycled portion of said stream is 0.1.

15. The process according to claim 1, wherein the stream comprising methane resulting from separating the product having a vapor pressure at 0° C. lower than 1 atmosphere from the stream comprising methane and the product having a vapor pressure at 0° C. lower than 1 atmosphere, additionally comprises unconverted ethylene and/or carbon oxides and is subjected to hydrogenation resulting in a stream comprising methane and optionally ethane.

16. The process according to claim 1, wherein the volume ratio of methane to ethane is from 0.2:1 to 100:1.

17. The process according to claim 1, wherein the volume ratio of methane to ethane is from 0.5:1 to 100:1.

18. The process according to claim 1, wherein the conversion of ethane is from 50 to 99.9%.

19. The process according to claim 1, wherein the conversion of ethane is from 60 to 99.9%.

20. The process according to claim 1, wherein the conversion of ethane is from 70 to 99.9%.

21. The process according to claim 1, wherein the conversion of ethane is from 70 to 90%.

22. The process according to claim 1, wherein the volume ratio of any recycled portion of the stream comprising methane and the product having a vapor pressure at 0° C. lower than 1 atmosphere to the non-recycled portion of said stream is 0:1 to 0.2:1.

23. The process according to claim 1, wherein the volume ratio of any recycled portion of the stream comprising methane and the product having a vapor pressure at 0° C. lower than 1 atmosphere to the non-recycled portion of said stream is 0:1.

* * * * *